(12) United States Patent
Wieloch et al.

(10) Patent No.: US 6,846,641 B2
(45) Date of Patent: Jan. 25, 2005

(54) IN VITRO ISCHEMIA MODEL

(75) Inventors: Tadeusz Wieloch, Lund (SE); Anna Rytter, Lund (SE); Tobias Cronberg, Lund (SE)

(73) Assignee: AGY Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 10/131,731

(22) Filed: Apr. 23, 2002

(65) Prior Publication Data

US 2003/0199086 A1 Oct. 23, 2003

(51) Int. Cl.$^7$ .......................... G01N 37/00; C12N 5/00; C12N 5/02
(52) U.S. Cl. .................. 435/7.21; 435/325; 435/368
(58) Field of Search ....................... 435/325, 352, 435/353, 354, 363, 366, 368, 404, 7.21

(56) References Cited

PUBLICATIONS

Robert et al. (Apr. 2002) "Blockade of NMDA–receptors or calcium–channels attenuates the ischaemia–evoked efflux of glutamate . . ." C.R. Biologies 325(4): 495–504.*
Whittingham et al. (Jun. 1992) "Glutamate–Induced Energetic Stress in Hippocampal Slices: Evidence Against NMDA and Glutamate Uptake as Mediators." Metabolic Brain Disease 7(2): 77–92.*
Tombaugh (Sep. 1994) "Mild Acidosis Delays Hypoxic Spreading Depression and Improves Neuronal Recovery in Hippocampal Slices." The Journal of Neuroscience 14(9): 5635–5643.*
Newman et al. (Jun. 1995) "Effects of K+, pH and glutamate on 45Ca kinetics in hippocampal brain slices." Journal of Neuroscience Methods 59(1): 111–120.*
Xiang & Bergold (Oct. 20, 2000) "Synaptic depression and neuronal loss in transiently acidic hippocampal slice cultures." Brain Research 881(1): 77–87.*
Yamane et al., Anaerobic Glycolysis is Crucial for the Maintenance of Neural Activity in Guinea Pig Hippocampal Slices, Journal of Neuroscience Methods, (2000), 103: 163–171.
Sochocka et al., Cell Death in Primary Cultures of Mouse Neurons and Astrocytes During Exposure to and 'Recovery' From Hypoxia, Substrate Deprivation and Simulated Ischemia, Brain Research, (1994), 638: 21–28.
Snider et al., Cycloheximide Reduces Infarct Volume When Administered Up to 6 H After Mild Focal Ischemia in Rats, Brain Research, (2001), 917: 147–157.
Siesjo et al., Pathophysiology and Treatment of Focal Cerebral Ischemia Part II: Mechanisms of Damage and Treatment, J. Neurosurg, (1992), 77: 337–354.

Reichert et al., The Mitochondrial Permeability Transition Pore and Nitric Oxide Synthase Mediate Early Mitochondrial Depolarization in Astrocytes During Oxygen–Glucose Deprivation, The Journal of Neuroscience, (2001), 21 (17): 5608–6616.
Pulsinelli et al., Temporal Profile of Neuronal Damage in a Model of Transient Forebrain Ischemia, American Neurological Association, (1981), 11: 491–498.
Koistinaho et al., Altered Gene Expression in Brain Ischemia, NeuroReport, (1997), 8 (2): 1–viii.
Kirinao et al., Delayed Neuronal Death in the Gerbil Hippocampus Following Ischemia, Brain Research, (1982), 239: 57–69.
Jin et al., Microarray Analysis of Hippocampal Gene Expression in Global Cerebral Ischemia, Ann. Neurol., (2001), 50: 93–103.
Hansen et al., Effect of Anoxia on Ion Distribution in the Brain, Physiological Reviews, (1985), 65: (1) 101–148.
Feuerstein et al., Inflammatory Gene Expression in Cerbral Ischemia and Trauma Potential New Therapeutic Targets, Annals New York Academy of Sciences, 825: 179–93.
Abdel–Hamid et al., Mechanisms and Effects of Intracellular Calcium Buffering on Neuronal Survival in Organotypic Hippocampal Cultures Exposed to Anoxia/Aglycemia or to Excitotoxins, The Journal of Neuroscience, 1997, 17(10): 3538–3553.
Striggow et al., The Protease Thrombin is an Endogenous Mediator of Hippocampal Neuroprotection Against Ischemia at Low Concentrations But Causes Degeneration at High Concentrations, PNAS, 2000, 97(5): 2264–2269.
Valazquez et al., In Vitro Ischemia Promotes Glutamate–Mediated Free Radical Generation and Intracellular Calcium Accumulation in Hippocampal Pyramidal Neurons, The Journal of Neuroscience, 1997, 17(23): 9085–9094.

* cited by examiner

*Primary Examiner*—Elizabeth Kemmerer
*Assistant Examiner*—Christopher James Nichols
(74) *Attorney, Agent, or Firm*—Pamela J. Sherwood; Bozicevic, Field & Francis LLP; Rebecca D. Taylor

(57) ABSTRACT

A tissue culture model of oxygen/glucose deprivation induced cell death is provided, which is useful in the analysis of the mechanisms of cell death following brain ischemia, and for screening anti-ischemic drugs. By adopting the in vivo concentrations of calcium, potassium and hydrogen ions to the incubation medium a model is established that shows conspicuous similarities with the temporal and special development of cell death in vivo: selective and delayed CA1 damage, a damage mitigated by blockade of the NMDA and AMPA receptors, and a striking augmentation of damage by high levels of glucose.

12 Claims, 10 Drawing Sheets

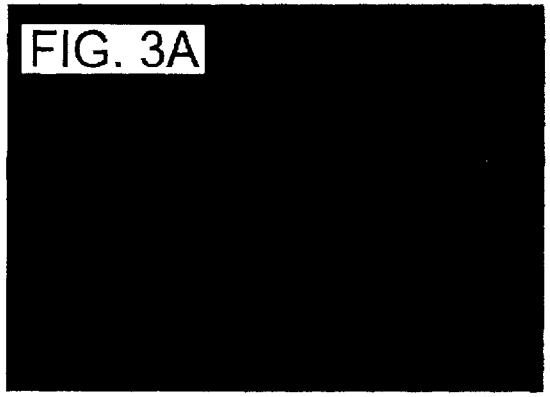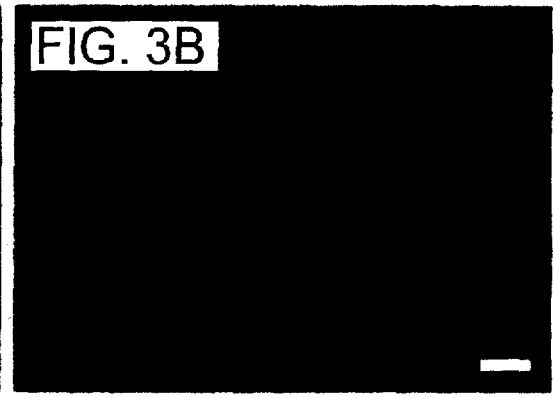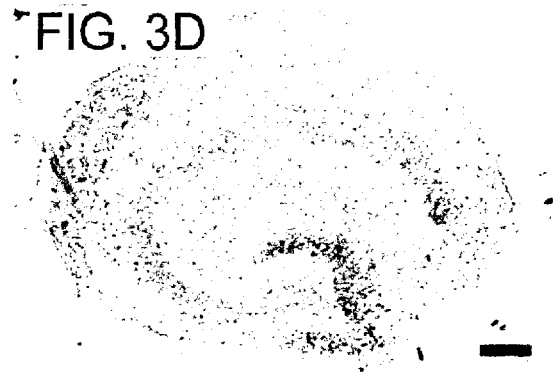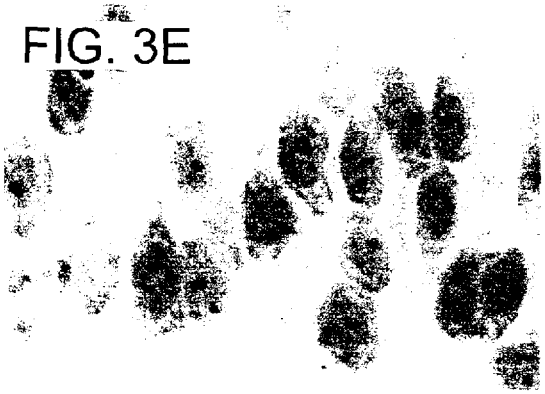

IN VITRO ISCHEMIA MODEL

BACKGROUND OF THE INVENTION

Neurodegenerative diseases are characterized by the dysfunction and death of neurons, leading to the loss of neurologic functions mediated by the brain, spinal cord and the peripheral nervous system. These disorders have a major impact on society. For example, approximately 4 to 5 million Americans are afflicted with the chronic neurodegenerative disease known as Alzheimer's disease. Other examples of chronic neurodegenerative diseases include diabetic peripheral neuropathy, multiple sclerosis, amyotrophic lateral sclerosis, Huntington's disease and Parkinson's disease. Normal brain aging is also associated with loss of normal neuronal function and may entail the depletion of certain neurons.

Though the mechanisms responsible for the dysfunction and death of neurons in neurodegenerative disorders are not well understood, a common theme is that loss of neurons results in both the loss of normal functions and the onset of adverse behavioral symptoms. Therapeutic agents that have been developed to retard loss of neuronal activity and survival have been largely ineffective. Some have toxic side effects that limit their usefulness. Other promising therapies, such as neurotrophic factors, are prevented from reaching their target site because of their inability to cross the blood-brain barrier.

Stroke is the third ranking cause of death in the United States, and accounts for half of neurology inpatients. Depending on the area of the brain that is damaged, a stroke can cause coma, paralysis, speech problems and dementia. The five major causes of cerebral infarction are vascular thrombosis, cerebral embolism, hypotension, hypertensive hemorrhage, and anoxia/hypoxia.

The brain requires glucose and oxygen to maintain neuronal metabolism and function. Hypoxia refers to inadequate delivery of oxygen to the brain, and ischemia results from insufficient cerebral blood flow. The consequences of cerebral ischemia depend on the degree and duration of reduced cerebral blood flow. Neurons can tolerate ischemia for 30–60 minutes, but perfusion must be reestablished before 3–6 hours of ischemia have elapsed. Neuronal damage can be less severe and reversible if flow is restored within a few hours, providing a window of opportunity for intervention.

If flow is not reestablished to the ischemic area, a series of metabolic processes ensue. The neurons become depleted of ATP and switch over to anaerobic glycolysis (Yamane et al. (2000) *J Neurosci Methods* 103(2):163–71). Lactate accumulates and the intracellular pH decreases. Without an adequate supply of ATP, membrane ion pumps fail. There is an influx of sodium, water, and calcium into the cell. The excess calcium is detrimental to cell function and contributes to membrane lysis. Cessation of mitochondrial function signals neuronal death (Reichert et al. (2001) *J Neurosci.* 21(17):6608–16). The astrocytes and oligodendroglia are slightly more resistant to ischemia, but their demise follows shortly if blood flow is not restored (Sochocka et al. (1994) *Brain Res* 638(1–2):21–8).

Evidence is also emerging in support of the possibility that acute inflammatory reactions to brain ischemia are causally related to brain damage. The inflammatory condition consists of cells (neutrophils at the onset and later monocytes) and mediators (cytokines, chemokines, others). Upregulation of proinflammatory cytokines, chemokines and endothelial-leukocyte adhesion molecules in the brain follow soon after an ischemic insult and at a time when the cellular component is evolving. The significance of the inflammatory response to brain ischemia is not fully understood (Feuerstein et al. (1997) *Ann NY Acad Sci* 825:179–93).

Studies in in vivo animal models of stroke, as well as in in vitro paradigms of ischemia-induced neuronal death, have shown that damage and dysfunction of neurons following ischemia is dependent on protein-synthesis (Jin et al. (2001) *Ann Neurol.* 50(1):93–103; Koistinaho et al. (1997) *Neuroreport* 8(2):i–viii). Thus, general proteinsynthesis inhibitors such as cycloheximide, and gene transcription blockers prevent ischemia-induced neuronal death (Snider et al. (2001) *Brain Res* 917(2):147–57). Therefore, the pathophysiology of ischemic stroke involves regulation of gene expression that ultimately result in neuronal death.

The integrated mechanisms of ischemic brain damage and the effect of drug interventions, are readily studied in rodent in vivo models of cerebral ischemia which for these purposes are more suitable than in vitro models. The intact brain preserves the blood-brain barrier and its interactions, and the complex neuronal networks and interactions among neurons and non-neuronal cells. On the other hand, the complexity does not permit detailed studies of particular molecular mechanisms and isolated cellular events. These limitations are overcome in the in vitro models of brain ischemia, were the contribution of blood components are eliminated and tissue temperature, extracellular environment, including ion and nutrient availability, can be standardized. Most in vitro models of ischemia have used a combination of oxygen and glucose deprivation (OGD) to imitate ischemic conditions in vivo (Sick and Somjen (1998) *Cerbrovascular disease* (Ginsberg M and Bogousslavsky J, eds.), Maiden: Blackwell Science, pp. 137–156). In these studies, the ionic content of the incubation medium, such as the artificial cerebrospinal fluid (aCSF), was similar to that found in normal brains.

However, it is also evident that the in vitro models do not fully reproduce the pathophysiological events that occur in the brain following in vivo ischemia. The hippocampus has been extensively studied following global ischemia in the rat and gerbil, and the damage is characterized by selective neuronal death in the CA1 region appearing 48–72 hours of recovery following 10–15 minutes of ischemia (Kirino (1982) *Brain Res* 239:57–69; Pulsinelli et al. (1982) *Ann Neurol* 11:491–498). However, although isolated hippocampal neurons in cultures or hippocampal tissue cultures are readily damaged by OGD, the temporal and special pattern of cell death is not similar to that seen in vivo.

One of the hallmarks of cerebral ischemia is the loss of ion homeostasis across cell membranes due to inhibition of adenosine triphosphate synthesis, which has been studied extensively in animal models of global and focal ischemia (Siesjo (1992) *J Neurosurg* 77:337–354). The membrane depolarization results in an increase in extracellular potassium, a decrease in extracellular calcium and a decrease in pH (Hansen (1985) *Physiol Rev* 65:101–148).

In view of the importance of neural disease and ischemia for human mortality and morbidity, the development of suitable models for in vitro screening and development is of great interest.

SUMMARY OF THE INVENTION

Methods and compositions are provided for in vitro culture of neural and/or brain tissue, which allow simulation of physiological and pathophysiological events. In one embodiment of the invention, the cells are an integrated system of brain tissue, with preserved synaptic connections and a diversity of cells including neurons, astrocytes and microglia. Such tissue can provide an in vitro model for pathophysiological events in the hippocampus following ischemia in vivo, including selective and delayed neuronal death in the CA1 region and increased damage by hyperglycemia.

The cell cultures of the invention find use in screening agents for their effect on neural cells and neurologic events, e.g. during ischemia. Such agents may include candidate drug compounds, genetic agents, e.g. coding sequences; polypeptides, e.g. factors, antibodies, etc.; and physiologic conditions, e.g. glucose, oxygen, etc. The cultured cells also find use as source of biological macromolecules, e.g. mRNA, proteins, etc., which may be associated with a neural event of interest.

BRIEF DESCRIPTION OF THE DRAWINGS

FIG. 3. Histological evaluation of cell damage. Control tissue culture (A,C,E) and a culture exposed to 15 min OGD in iCSF and 48 hrs recovery (B,D,F), were stained with propidium iodide (A,B) and sectioned at 2.5 $\mu$m and stained with methylene blue/azurblue (C–F). In control culture no cell death is seen (A), while OGD induces approximately 25% damage in the CA1 region (B). The pyramidal cell bands and dentate gyrus are clearly visible in the control culture (C) and more diffuse in the OGD exposed cultures (D). In higer magnification, condensed nuclei are accumulating after OGD (F) but not in control (E). Scale bars: 200 $\mu$m in A–D and 10 $\mu$m in E and F.

DETAILED DESCRIPTION OF THE EMBODIMENTS

Figure 1:
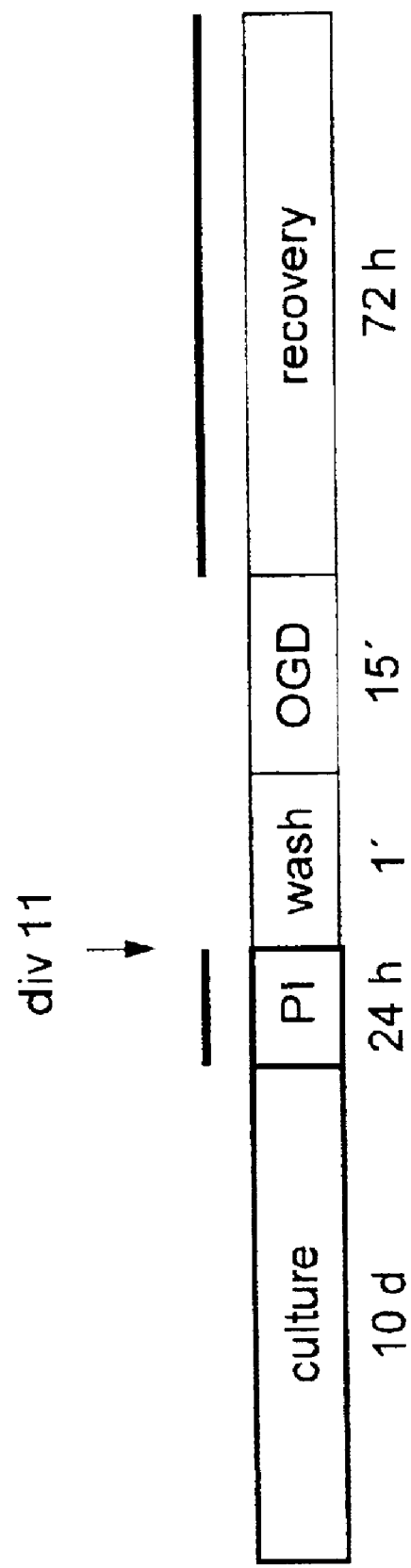
FIG. 1. Protocol for oxygen and glucose deprivation experiments in mouse hippocampal organotypic cultures. Organotypic cultures were grown for eleven days before experiments. Propidium iodide (1 $\mu$g/ml) was added to the culture medium 24 hours before the start of OGD and maintained throughout the experiment. Cultures were washed once before the induction of OGD. Images were captured at variable time-points during the 72 hours of recovery.

Methods and compositions are provided for in vitro culture of neural and/or brain tissue. The conditions and culture medium allow simulation of physiological and pathophysiological events affecting neural cells. Cultures of suitable cells are exposed transiently to a synthetic medium that reproduces the effects of ischemia. The cells are then monitored for the effect of the ischemic conditions on physiology, phenotype, etc.

In one embodiment of the invention, the cells are an integrated system of brain tissue, with preserved synaptic connections and a diversity of cells including neurons, astrocytes and microglia. Such tissue can provide an in vitro model for pathophysiological events in the hippocampus following ischemia in vivo, including selective and delayed neuronal death in the CA1 region and increased damage by hyperglycemia.

The cell cultures of the invention find use in screening agents for their effect on neural and/or brain cells and neurologic events, e.g. during ischemia. Such agents may include candidate drug compounds, genetic agents, e.g. coding sequences; polypeptides, e.g. factors, antibodies, etc.; and physiologic conditions, e.g. glucose, oxygen, etc. The cultured cells also find use as source of biological macromolecules, e.g. mRNA, proteins, etc., which may be associated with a neural event of interest.

Oxygen and glucose deprivation (OGD) in cell cultures has been studied in the past by exposing cultured tissue to media such as artificial cerebro-spinal fluid (aCSF), with an ion composition similar to that of the extracellular fluid of normal brain, with 2–4 mM $K^+$, 2–3 mM $Ca^{2+}$ and pH 7.4. However, during ischemia the distribution of ions across cell membranes dramatically shift. The present invention provides a medium that more accurately reflects the extracellular fluid of the brain during an ischemic event.

Artificial ischemic cerebro-spinal fluid (iCSF), as used herein, refers to a glucose-free medium similar to the extracellular fluid of the brain during ischemia in vivo. The iCSF ionicity has a potassium concentration of at least about 50 mM, not more than about 90 mM, usually at least about 60 mM, not more than about 80 mM, and preferably about 65 to 75 mM $K^+$, and in some instances about 70 mM $K^+$. The concentration of calcium is at least about 0.1 mM, not more than about 1 mM, usually at least about 0.2 mM and not more than about 0.5 mM, preferably about 0.3 mM $Ca^{2+}$. The pH of the iCSF media is at least about 6.7 and not more than about 6.9, preferably about pH 6.8.

The medium may be glucose free, or may comprise glucose at a concentration of from about 10 mM to 100 mM, usually from about 25 mM to 75 mM, and may be about 40 mM. The cultures of the present invention show increased cell damage in the presence of glucose during ischemia, which simulates the in vivo effects of glucose. Hyperglycemia aggravates ischemic brain damage in vivo, and glucose in iCSF also significantly exacerbates cell damage-following oxygen deprivation. This model of in vitro ischemia is useful in studies of the mechanisms and treatment of ischemic cell death.

The cells are maintained in the ischemic conditions for a period of time sufficient to induce a detectable effect, usually for at least about 5 minutes, more usually for at least about 1 minutes, preferable for at least about 15 minutes, and for not more than about 1 hour.

Maintaining cultured cells in vitro in iCSF during oxygen glucose deprivation (OGD) provides a realistic simulation of in vivo events, which include a selective and delayed cell death in the CA1 region, assessed by propidium iodide uptake. Cell death is glutamate receptor dependent, as evidenced by the mitigation of damage by blockade of the N-methyl-D-aspartate and the α-Amino-3-hydroxy-5-methyl-4-isoxazolepropionic acid receptors.

Screening methods generally involve conducting various types of assays to identify agents that affect tissue damage that occurs during ischemia. Lead compounds identified during these screens can serve as the basis for the synthesis of more active analogs. Lead compounds and/or active analogs generated therefrom can be formulated into pharmaceutical compositions effective in treating neurological disorders such as stroke, epilepsy and neurodegenerative disorders.

Disease Conditions

"Neurologic disorder" is defined here and in the claims as a disorder in which dysfunction and loss of neurons occurs either in the peripheral nervous system or in the central nervous system. Examples of neurologic disorders include: chronic neurodegenerative diseases such as Alzheimer's disease, Parkinson's disease, Huntington's chorea, diabetic peripheral neuropathy, multiple sclerosis, amyotrophic lateral sclerosis, aging, and acute disorders including: stroke, traumatic brain injury, peripheral nerve damage, hypoglycemia, spinal cord injury, epilepsy, and anoxia and hypoxia.

The term "stroke" broadly refers to the development of neurological deficits associated with impaired blood flow to the brain regardless of cause. Potential causes include, but are not limited to, thrombosis, hemorrhage and embolism. Current methods for diagnosing stroke include symptom evaluation, medical history, chest X-ray, ECG (electrical heart activity), EEG (brain nerve cell activity), CAT scan to assess brain damage and MRI to obtain internal body visuals. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardic arrest, cardiogenic shock, septic shock, head trauma, spinal cord trauma, seizure, bleeding from a tumor, or other blood loss.

By "ischemic episode" is meant any circumstance that results in a deficient supply of blood to a tissue. When the ischemia is associated with a stroke, it can be either global or focal ischemia, as defined below. The term "ischemic stroke" refers more specifically to a type of stroke that is of limited extent and caused due to blockage of blood flow. Cerebral ischemic episodes result from a deficiency in the blood supply to the brain. The spinal cord, which is also a part of the central nervous system, is equally susceptible to ischemia resulting from diminished blood flow.

By "focal ischemia," as used herein in reference to the central nervous system, is meant the condition that results from the blockage of a single artery that supplies blood to the brain or spinal cord, resulting in damage to the cells in the territory supplied by that artery.

By "global ischemia," as used herein in reference to the central nervous system, is meant the condition that results from a general diminution of blood flow to the entire brain, forebrain, or spinal cord, which causes the death of neurons in selectively vulnerable regions throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension.

Stroke can be modeled in animals, such as the rat (for a review see Duverger et al. (1988) *J Cereb Blood Flow Metab*

8(4):449–61), by occluding certain cerebral arteries that prevent blood from flowing into particular regions of the brain, then releasing the occlusion and permitting blood to flow back into that region of the brain (reperfusion). These focal ischemia models are in contrast to global ischemia models where blood flow to the entire brain is blocked for a period of time prior to reperfusion. Certain regions of the brain are particularly sensitive to this type of ischemic insult. The precise region of the brain that is directly affected is dictated by the location of the blockage and duration of ischemia prior to reperfusion.

Neural Cell Cultures

The ischemic medium of the present invention may be used with any neural or brain cell culture. The cells may be primary cultures that are set up for short term growth. Such primary cultures can provide highly reproducible results from one culture to another. Alternatively, cell lines are used. Cell lines are generally able to be passaged in culture for extended periods of time. Examples of cultured excitable cells include, but are not limited to, suprachiasmatic neurons (Walsh et al. (1995) *Neuroscience* 69(3):915–29); motoneuronal cultures (Zoran et al. (1996) *Dev Biol* 179(1):212–22).

In a preferred embodiment, the cultured cells comprise a section of brain tissue, e.g. sections of hippocampus, cerebral cortex, cerebellum, spinal cord, and the like. Section may be taken by conventional methods, typically of a width sufficient to provide viable cells of diverse types, i.e. from about 100 $\mu$m to 1000 $\mu$M, usually from about 200 $\mu$m to about 500 $\mu$m. The cells are maintained in vitro in suitable medium, e.g. MEM, RPMI, etc., usually in the presence of serum or serum replacement at a concentration of from about 5% to 50%. Suitable conditions are known in the art, and are further provided in the examples.

For various purposes it is desirable to utilize cells comprising an altered complement of ion channels, either through deletion or addition of expressed channel genes. Such genetic manipulation may be performed in vitro, on cultured cells, particularly where the cells are maintained as a long term cell line. Alternatively, transgenic animals may be constructed or commercially obtained. Cells and tissues derived from such transgenic animals are used a source of cells for primary cultures. Methods of creating transgenic animals, either knock-outs or knock-ins, are well known in the art and need not be discussed in further detail herein.

The term "environment," or "culture condition" encompasses cells, media, factors, time and temperature. Environments may also include drugs and other compounds, particular atmospheric conditions, pH, salt composition, minerals, etc. The conditions will be controlled. Culture of cells is typically performed in a sterile environment, for example, at 37° C. in an incubator containing a humidified 92–95% air/5–8% $CO_2$ atmosphere.

The cell surface expression of various surface and intracellular markers, including protein, lipid; nucleic acid, e.g. genetic markers; and carbohydrate is known for a large number of different types of cells, and can be used as a reference for establishing the exact phenotype of cells in vivo; for determining whether that same phenotype is present in the cultured cells, for determining the effect of an agent, particularly a pharmacologic agent, on the cells, and the like. The manner in which cells respond to an agent, particularly a pharmacologic agent, including the timing of responses, is an important reflection of the physiologic state of the cell.

Parameters are quantifiable components of cells, particularly components that can be accurately measured. A parameter can be any cell property, e.g. viability; component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g. polypeptides, polysaccharides, polynucleotides, lipids, etc. A parameter may be detection of a specifically modified protein or oligosaccharide, e.g. a phosphorylated protein. The presence of the active conformation of a receptor may comprise one parameter while an inactive conformation of a receptor may comprise another.

Screening Methods

Agents are screened for biological activity by adding the agent to an ischemic cell culture before, during or after induction of ischemic conditions. When the agent is added prior to induction of ischemia, it may be added several days prior to induction, one day prior, up to immediately prior to induction. Agents added after induction will usually be added shortly after, within at least about 24 hours, up to immediately after completion of the ischemic episode. The change in parameter readout in response to the agent is measured, and compared to a control culture. Suitable controls include known mitigating agents, known damaging agents, an absence of any exogenous agents, and the like. Agents of interest for analysis include any biologically active molecule with the capability of modulating, directly or indirectly, the phenotype of interest.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected parameters. For measuring the amount of a molecule that is present, a convenient method is to label a molecule with a detectable moiety, which may be fluorescent, luminescent, radioactive, enzymatically active, etc., particularly a molecule specific for binding to the parameter with high affinity Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477–81). Thus, antibodies can be genetically modified to provide a fluorescent dye as part of their structure.

Multiple fluorescent labels can be used on the same sample and individually detected quantitatively, permitting measurement of multiple cellular responses simultaneously. Many quantitative techniques have been developed to harness the unique properties of fluorescence including: direct fluorescence measurements, fluorescence resonance energy transfer (FRET), fluorescence polarization or anisotropy (FP), time resolved fluorescence (TRF), fluorescence lifetime measurements (FLM), fluorescence correlation spectroscopy (FCS), and fluorescence photobleaching recovery (FPR) (Handbook of Fluorescent Probes and Research Chemicals, Seventh Edition, Molecular Probes, Eugene Oreg.).

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112–225; Kawamoto et al. (1999) Genome Res 9(12):1305–12; and Chen et al. (1998) Genomics 51 (3):313–24, for examples.

The level of expression or activity can be compared to a baseline value. Te baseline value can be a value for a control sample or a statistical value that is representative of expression levels for a control population. Such cells generally are otherwise substantially genetically the same as the test cells. Various controls can be conducted to ensure that an observed activity is authentic.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

The data from cells treated with specific drugs known to interact with particular targets or pathways provide a more detailed set of readouts for analysis. For example, data generated from cells that are genetically modified using over-expression techniques and anti-sense techniques, permit testing the influence of individual genes on the phenotype.

Compounds that are initially identified by any of the foregoing screening methods can be further tested to validate the apparent activity. The basic format of such methods involves administering a lead compound identified during an initial screen to an animal that serves as a model for humans and then determining the phenotype of affected cells. The animal models utilized in validation studies generally are mammals. Specific examples of suitable animals include, but are not limited to, primates, mice, and rats.

Active test agents identified by the screening methods described herein that affect ischemia can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Once analogs have been prepared, they can be screened using the methods disclosed herein to identify those analogs that exhibit an increased ability to modulate ischemia. Such compounds can then be subjected to further analysis to identify those compounds that have the greatest potential as pharmaceutical agents. Alternatively, analogs shown to have activity through the screening methods can serve as lead compounds in the preparation of still further analogs, which can be screened by the methods described herein. The cycle of screening, synthesizing analogs and re-screening can be repeated multiple times.

Candidate Agents

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, ie. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 $\mu$l to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Genetic Agents

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; encode a dominant negative mutation, or dominant or constitutively active mutations of native sequences; altered regulatory sequences, etc.

A large number of public resources are available as a source of genetic sequences, e.g. for human, other mammalian, and human pathogen sequences. A substantial portion of the human genome is sequenced, and can be accessed through public databases such as Genbank. Resources include the uni-gene set, as well as genomic sequences. For example, see Dunham et al. (1999) *Nature* 402, 489–495; or Deloukas et al. (1998) *Science* 282, 744–746.

cDNA clones corresponding to many human gene sequences are available from the IMAGE consortium. The international IMAGE Consortium laboratories develop and array cDNA clones for worldwide use. The clones are commercially available, for example from Genome Systems, Inc., St. Louis, Mo. Methods for cloning sequences by PCR based on DNA sequence information are also known in the art.

Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence. Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc.

In mammalian host cells, a number of viral-based expression systems may be utilized, e.g. retrovirus, lentivirus, adenovirus, herpesvirus, and the like. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Natl. Acad. Sci. USA 81:3655–3659). Specific initiation signals may also be required for efficient translation of inserted gene product coding sequences. These signals include the ATG initiation codon and adjacent sequences. Standard systems for generating adenoviral vectors for expression on inserted sequences are available from commercial sources, for example the Adeno-X™ expression system from Clontech (Clontechniques (January 2000) p. 10–12).

In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In one embodiment, the genetic agent is an antisense sequence that acts to reduce expression of the complementary sequence. Antisense nucleic acids are designed to specifically bind to RNA, resulting in the formation of RNA-DNA or RNA-RNA hybrids, with an arrest of DNA replication, reverse transcription or messenger RNA translation. Antisense molecules inhibit gene expression through various mechanisms, e.g. by reducing the amount of mRNA available for translation, through activation of RNAse H, or steric hindrance. Antisense nucleic acids based on a selected nucleic acid sequence can interfere with expression of the corresponding gene. Antisense nucleic acids can be generated within the cell by transcription from antisense constructs that contain the antisense strand as the transcribed strand.

The anti-sense reagent can also be antisense oligonucleotides (ODN), particularly synthetic ODN having chemical modifications from native nucleic acids, or nucleic acid constructs that express such anti-sense molecules as RNA. One or a combination of antisense molecules may be administered, where a combination may comprise multiple different sequences. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

As an alternative method, dominant negative mutations are readily generated for corresponding proteins. These may act by several different mechanisms, including mutations in a substrate-binding domain; mutations in a catalytic domain; mutations in a protein binding domain (e.g. multimer forming, effector, or activating protein binding domains); mutations in cellular localization domain, etc.

Identification of Differential Gene Expression

The cultured cells may be used as a source of biological macromolecules, particularly for the analysis of differential gene expression, e.g. to isolate mRNA, polypeptides, etc. in order to determine the effects of ischemia on the cells. Differentially expressed genes are detected by comparing the pattern of gene or polypeptide expression between the experimental and control conditions. Once a particular sequence is identified, the expression pattern may be further characterized by sequencing, proteomic analysis, microarray hybridization, and the like. Differential expression and expression patterns of induced genes may be confirmed by in situ hybridization or RT-PCR on tissue generated from ischemic models.

"Differential expression" as used herein refers to both quantitative as well as qualitative differences in the genes' temporal and/or tissue expression patterns. Thus, a differentially expressed gene may have its expression activated or completely inactivated in normal versus neuronal disease conditions, or under control versus experimental conditions. Such a qualitatively regulated gene will exhibit an expression pattern within a given tissue or cell type that is detectable in either control or neuronal disease subjects, but is not detectable in both. Detectable, as used herein, refers to an RNA expression pattern that is detectable via the standard techniques of differential display, reverse transcriptase-(RT-) PCR and/or Northern analyses, which are well known to those of skill in the art. Generally, differential expression means that there is at least a 20% change, and in other instances at least a 2-, 3-, 5- or 10-fold difference between disease and control tissue expression. The difference usually is one that is statistically significant, meaning that the probability of the difference occurring by chance (the P-value) is less than some predetermined level (e.g., 0.05). Usually the confidence level P is <0.05, more typically <0.01, and in other instances, <0.001.

Alternatively, a differentially expressed gene may have its expression modulated, i.e., quantitatively increased or decreased, in normal versus neuronal disease states, or under control versus experimental conditions. The difference in expression need only be large enough to be visualized via standard detection techniques as described above.

Once a sequence has been identified as differentially expressed, the sequence can be subjected to a functional validation process to determine whether the gene plays a role in ischemia. Such candidate genes can potentially be correlated with a wide variety of cellular states or activities, including protective responses to an ischemic episode. The term "functional validation" as used herein refers to a process whereby one determines whether modulation of expression of a candidate gene or set of such genes causes a detectable change in a cellular activity or cellular state for a reference cell, which cell can be a population of cells such as a tissue or an entire organism. The detectable change or alteration that is detected can be any activity carried out by the reference cell. Specific examples of activities or states in which alterations can be detected include, but are not limited to, phenotypic changes (e.g., cell morphology, cell proliferation, cell viability and cell death); cells acquiring resistance to a prior sensitivity or acquiring a sensitivity which previously did not exist; protein/protein interactions; cell movement; intracellular or intercellular signaling; cell/cell interactions; cell activation (e.g., T cell activation, B cell activation, mast cell degranulation); release of cellular components (e.g., hormones, chemokines and the like); and metabolic or catabolic reactions.

A variety of options are available for functionally validating candidate genes identified. Such methods as interference RNA (RNAi) technology can be used. In this approach, a molecule of double-stranded RNA specific to a target gene is used. Antisense technology can also be utilized to functionally validate a candidate gene. In this approach, an antisense polynucleotide that specifically hybridizes to a segment of the coding sequence for the candidate gene is administered to inhibit expression of the candidate gene in those cells into which it is introduced. The functional role that a candidate gene plays in a cell can also be assessed using gene "knockout" approaches in which the candidate gene is deleted, modified, or inhibited on either a single or both alleles. The cells or animals can be optionally be reconstituted with a wild-type candidate gene as part of a further analysis.

In one embodiment of the invention, RNAi technology is used in functional validation. As used herein, RNAi technology refers to a process in Which doubles tranded RNA is introduced into cells expressing a candidate gene to inhibit expression of the candidate gene, i.e., to "silence" its expression. The dsRNA is selected to have substantial identity with the candidate gene. In general such methods initially involve in vitro transcription of a nucleic acid molecule containing all or part of a candidate gene sequence into single-stranded RNA. Sense and anti-sense RNA strands are allowed to anneal under appropriate conditions to form dsRNA. The resulting dsRNA is introduced into reference cells via various methods and the degree of attenuation in expression of the candidate gene is measured using various techniques. Usually one detects whether inhibition alters a cellular state, cellular activity or cellular phenotype. The dsRNA is prepared to be substantially identical to at least a segment of a candidate gene. Because only substantial sequence similarity between the candidate gene and the dsRNA is necessary, sequence variations between these two species arising from genetic mutations, evolutionary divergence and polymorphisms can be tolerated. Moreover, the dsRNA can include various modified or nucleotide analogs. Usually the dsRNA consists of two separate complementary RNA strands. However, in some instances, the dsRNA may be formed by a single strand of RNA that is self-complementary, such that the strand loops back upon itself to form a hairpin loop. Regardless of form, RNA duplex formation can occur inside or outside of a cell.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

Once the dsRNA has been formed, it is introduced into a cell. For example, a neuroblastoma-derived cell line can serve as a model system for investigating genes that are correlated with various neurological diseases. Examples of diseases that can be studied with this particular cell line include, but are not limited to, Alzheimer's disease, Parkinson's disease, brain tumor, epilepsy, stroke, especially ischemic stroke, and other neurodegenerative diseases.

A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133–1137; and Wianny, et al. (1998) Chromosoma 107:430–439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

A number of options are available to detect interference of candidate gene expression (i.e., to detect candidate gene silencing). In general, inhibition in expression is detected by detecting a decrease in the level of the protein encoded by the candidate gene, determining the level of mRNA transcribed from the gene and/or detecting a change in phenotype associated with candidate gene expression.

Pharmaceutical Compositions

Compounds identified by the screening methods described above and analogs thereof can serve as the active ingredient in pharmaceutical compositions formulated for the treatment of various neurological disorders, including stroke. The compositions can also include various other agents to enhance delivery and efficacy. For instance, compositions can include agents capable of increasing the permeability of the blood/brain barrier. The compositions can also include various agents to enhance delivery and stability of the active ingredients.

Thus, for example, the compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527–1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides or paraffin hydrocarbons. In addition, it is also possible to use gelatin rectal capsules which consist of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLE 1

Materials and Methods

Preparation and maintenance of organotypic hippocampal tissue cultures. All animal experiments were approved by the Malmoe/Lund ethical committee on animal experiments. Organotypic hippocampal cultures were prepared according to Stoppini et al. (1991) *J Neurosci Methods* 37:173–182 with some modifications. Brains of 6-day-old Balb/c mice were removed and gently immersed into ice-cold dissection medium containing HBSS (Hank's balanced salt solution) with 20 mM HEPES, 100 units Penicillin-Streptomycin/ml and 41.5 mM D-glucose. Hippocampi were dissected out on ice and cut into 250 μm thick transverse sections using a McIlwain Tissue Chopper. Cultures with even margins and clear, uniform and well defined pyramidal cell layers were selected and plated onto Millicell culture inserts (0.4 μm Millicell-CM, 12 mm in diameter, Millipore), one culture per insert. Sections from the caudal and most frontal parts of the hippocampus were discarded. Cultures were maintained at 35° C., 90–95% humidity in a $CO_2$ incubator (Forma Scientific) for 10–11 days before experiments.

The culture medium consisted of 50% MEM (Eagles with Earl's balanced salt solution), 25% heat inactivated horse serum, 18% HBSS supplemented with 1×B27, 4 mM L-glutamine, 50 units Penicillin-Streptomycin/ml, 6 mg/ml (40 mM) d-glucose. The pH was adjusted to 7.4 with sodium bicarbonate. Culture medium was changed on the second day in vitro (div 2) and then every other day. All substances used for preparation and maintenance of cultures were obtained from GibcoBRL, Life Technologies, with the exception of D-glucose, which was from Sigma.

Histological evaluation of cultures. For histology the cultures were washed in phosphate-buffered saline (PBS), fixed in 4% paraformaldehyde in PBS for 1 hour at room temperature and then stored in PBS at 4° C. Cultures on their membranes were dehydrated and embedded in Agar100 (LinkNordiska, Sweden). Cultures were cut out of the insert and sectioned into 2.5 μm thick sections on a ultratome. Sections were then stained with 0.5% methyleneblue/0.5% azurblue dissolved in 1% borax.

Electrophysiological experiments. For electrophysiological recordings the slice on its membrane was placed in a recording chamber and submerged in aCSF consisting of (in mM): 119 NaCl, 2.5 KCl, 1.3 $MgSO_4$, 2.5 $CaCl_2$, 26.2 $NaHCO_3$, 1 $NaH_2PO_4$ and 11 glucose, which was gassed with 95% $O_2$—5% $CO_2$ The temperature of the recording chamber was kept between 21–23° C. Extracellular field EPSPs were recorded via a glass pipette containing 3M NaCl (0.5–1 MΩ). Field potentials were amplified and filtered at 1 kHz and sampled at 10 kHz with an EPC-9 patch-clamp amplifier (HEKA Electronics, Lambrecht, Germany), and stored on a Power Macintosh computer for offline analysis. The amplitude of the field EPSP at its peak was measured over a period of 1–2 ms. Both recording and stimulating electrodes were placed under visual guidance in the stratum radiatum (stimulating and extracellular recording electrodes) or in the cell layer (whole-cell recording pipettes) of the CA1 region. Whole-cell recording pipettes (4–6 MΩ) were filled with the following (in mM): 122.5 K gluconate, 17.5 KCl, 10 HEPES, 0.2 EGTA, 8 NaCl, 2 MgATP, and 0.3 GTP (pH 7.2, osmolarity 295 mOsm). Both current-clamp and voltage-clamp recordings were used. Membrane currents were amplified and filtered at 2.9 kHz and sampled at 10 kHz with an EPC-9 patch-clamp amplifier. The holding potential was −80 mV for recording AMPA receptor-mediated EPSCs and +30 mV for recording NMDA receptor-mediated EPSCs. Junctional potentials were not corrected.

Induction of OGD. All cultures used in one experiment were prepared from mice pups from 1–3 females with litters born on the same day. Cultures were grown for 10–11 days and grouped before experiment so that each experimental group contained cultures from six different pups. Cultures showing distinct PI uptake in the pyramidal cell band were excluded. A scarce PI uptake was sometimes observed in the dorsal blade of the dentate gyrus. Prior to OGD, cultures were washed once in glucose free medium and transferred to the anaerobic incubator. The anaerobic incubator (Elektrotek ltd., England), equipped with a palladium catalyst to remove traces of oxygen, was custom made for the hypoxia experiments and had an aperture for rapid entry of 24-well-plates. It had an atmosphere of 10% $H_2$, 5% $co_2$ and 85% $N_2$ and the temperature was maintained at 35.0±0.3° C. Inside the incubator cultures were transferred to wells containing OGD-medium, which had been placed in the anaerobic atmosphere overnight or bubbled with the anoxic gas mixture for at least one hour before use. OGD was terminated when cultures were transferred to new wells with oxygenated culture medium and then transferred to the $co_2$ incubator. Culture-controls were maintained in the $co_2$ incubator throughout the experiment.

Two OGD-mediums were used: aCSF with the following composition: (in mM): 2 $CaCl_2$, 125 NaCl, 25 $NaHCO_3$, 2.5 KCl; 1.25 $NaH_2PO_4$, 2 $MgSO_4$, 10 sucrose, pH 7.4 and iCSF with: 0.3 $CaCl_2$; 70 NaCl; 5.25 $NaHCO_3$; 70 KCl; 1.25 $NaH_2PO_4$; 2 $MgSO_4$, 10 sucrose, pH 6.8. For studies of glutamate receptors 20 μM of the non-competitive N-methyl-D-aspartate (NMDA)-receptor antagonist dizocilpine maleate (MK-801) was added to the culture medium one hour before OGD. The competitive NMDA receptor antagonist D-2 amino-5-phosphonopentanoic-acid (D-AP5, 150 μM) and the α-Amino-3-hydroxy-5-methyl-4-isoxazolepropionic acid (AMPA)-receptor blocker 2,3-Dihydro-6-nitro-7-sulphamoyl-benzo (F) quinoxaline (NBQX, 100 μM) were added to the medium one hour before OGD, to the OGD medium and to the culture medium during the 24-hour recovery period. MK-801 was purchased from Sigma, D-AP5 and NBQX-disodium salt from Tocris.

Quantification of cell damage. Propidium iodide (PI) (1 μg/ml) was added to the medium the day before the insult and was included throughout the duration of the experiment (FIG. 1). Cultures were examined with an inverted fluorescence microscope. Excitation was at 510–550 nm and emission was at 590 nm and above. Images were captured using a 12-bit monochrome cooled fluorescence camera (Apogee Instruments, U.S.A.) and processed with Image-Pro Plus 4.0 software (Media Cybernetics, Maryland, U.S.A.).

Figure 2:
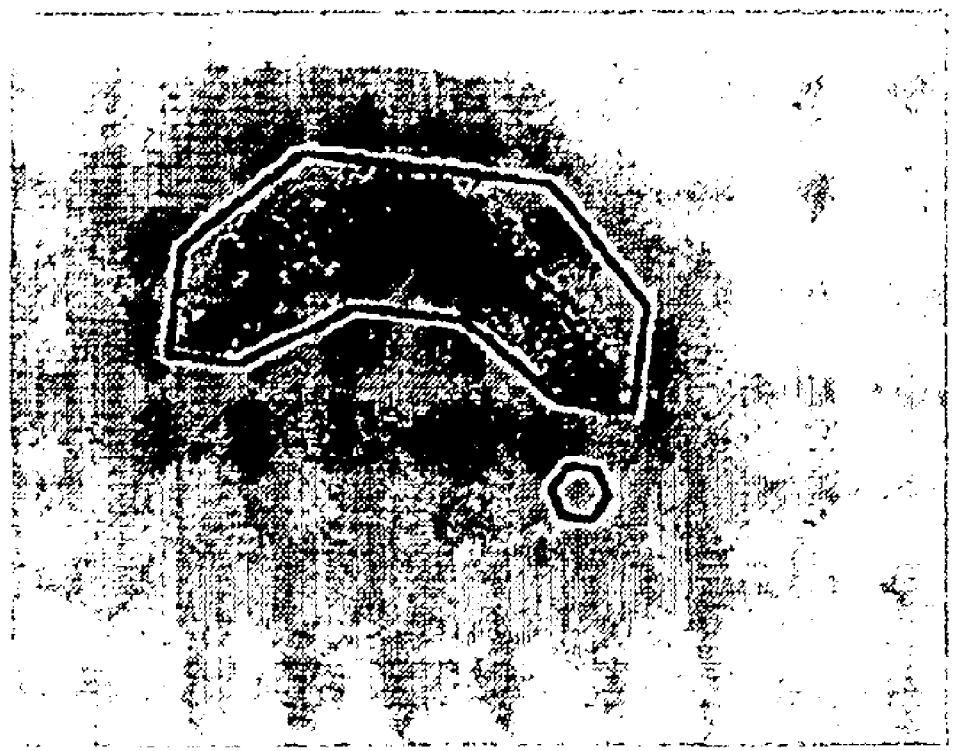
FIG. 2. Method for quantification of cell damage. Inverted fluorescence image of a propidium iodide (PI)-stained cell culture 48 hours after OGD. PI-intensity is measured as mean fluorescence intensity (MFI) in a standardized area in the CA1 region as indicated. Background MFI is measured in a standardized hexagon area in the CA2–CA3 region and subtracted from the MFI measured in the CA1 area.

Measurements of cell damage were made on PI-fluorescence images. Images were obtained prior to and 4, 8, 12, 24, 48 and 72 hours after the insult. Fluorescence intensity was measured in a standardized area (FIG. 2), in CA1. At all time points a faint, diffuse staining was observed throughout the pyramidal cell layer. Background staining was measured in a small hexagon placed in the CA2/CA3 region where no damage was observed. As this background staining increased with time, it was subtracted from the value measured in the standardized CA1 area. Values are expressed as mean fluorescence intensity (MFI).

Statistics. For statistical analyses the commercial software Statview 4.0 (Abacus Concepts Inc, Berkley, Calif., U.S.A.) was used. Data are expressed as mean±SD. All statistical groups consist of data obtained from at least three separate experiments. All compared groups were run in parallel inside the anaerobic incubator. Analysis of variance (ANOVA) with Fisher's post-hoc test was used to evaluate differences between groups. Variability between experimental dates was compensated for by including date as a factor.

Results

Characteristics of the mouse hippocampal organotypic tissue culture. FIG. 3 shows sections of hippocampal organotypic tissue cultures (div 13) stained with PI (A and B) and with methylene blue/azure blue (C–F). Photomicrographs of control cultures (A,C,E) are from the same tissue culture, and (B,D,F) is a culture exposed to 15 min OGD in iCSF and 48 h recovery. The cultures have preserved their organotypic appearance and the pyramidal and granule cell layers are clearly visible (FIG. 3C and D). In control cultures the pyramidal cell bodies have a typical owl's eye look and the neuropil is compact with no evident swollen structures (FIG. 3E). Following OGD, damage to CA1 neurons is seen as a clearing of the cell body layer, while cells in CA3 are intact. In the CA1 region, dead neurons are pycnotic with dark condensed nuclei, among surviving neurons (FIG. 3E). Approximately 25% cell death is seen following 15 min OGD in iCSF.

Figure 4A:
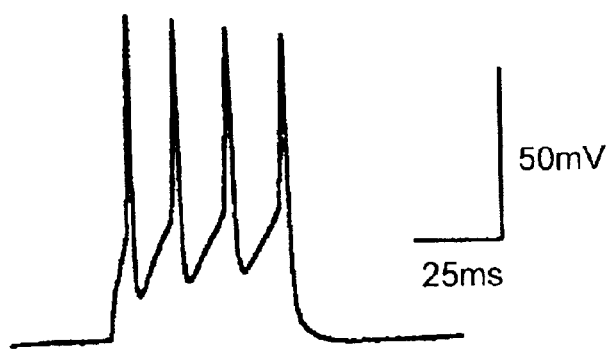
FIG. 4. Electrophysiological characteristics of CA1 pyramidal cells in mouse hippocampal organotypic tissue cultures. (A) Spike activity in a CA1 pyramidal cell induced by step depolarization. (B) Recordings of spontaneous EPSCs from a CA1 pyramidal cell. (C) Averaged evoked EPSCs (10 traces) recorded in CA1 pyramidal cell clamped at –80 mV (left) and at +30 mV with NBQX (5 $\mu$M)(right). (D) Long-lasting increase in synaptic efficacy induced by a high-frequency stimulation (HFS, two 100-impulse trains, 100 Hz 20 sec apart) representative field responses (average of five) taken before (a) and after (b) the HFS.
Figure 4B:
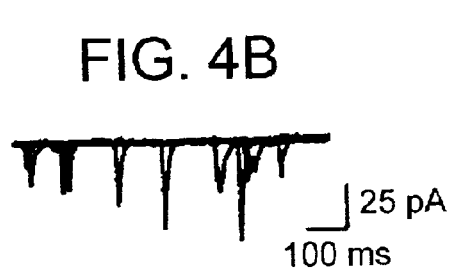
Figure 4C:
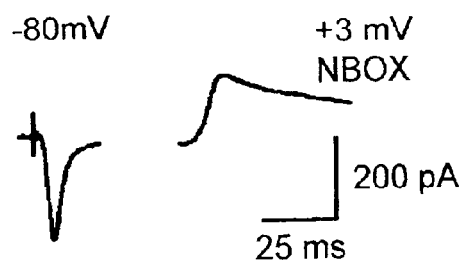
Figure 4D:
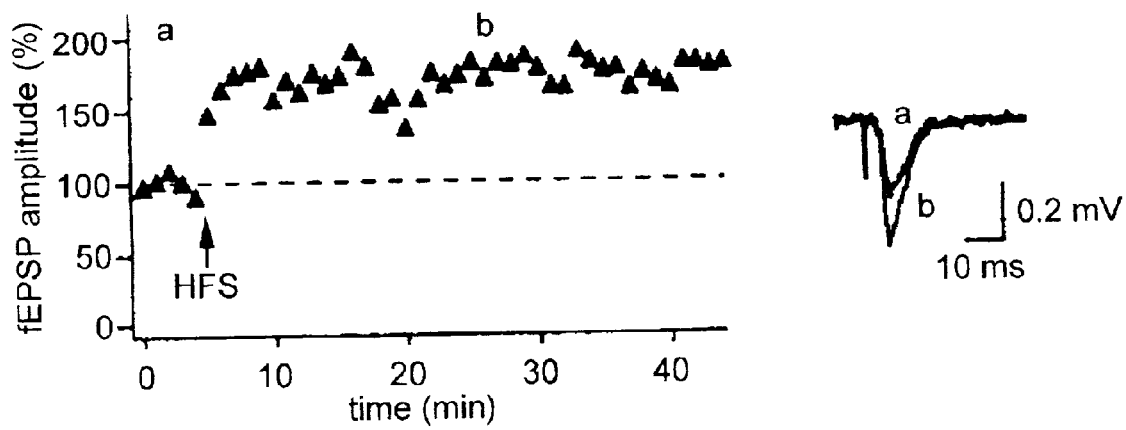

In order to assess whether the culture conditions affect the properties of the mouse hippocampal organotypic tissue culture, the electrophysiological properties of CA1 neurons were investigated. Using whole cells recordings in current-clamp mode it was found that all cells tested were able to fire action potentials in response to depolarizing current injections (FIG. 4A). In voltage-clamp mode, clamping the cell at −80 mV, and blocking inhibitory synaptic activity with the $GABA_A$ antagonist picrotoxin, spontaneous excitatory synaptic currents were recorded (FIG. 4B). When evoking excitatory synaptic signals by activating the Schaffer collaterals we could obtain both AMPA- and NMDA-receptor mediated synaptic signals (FIG. 4C). Also spontaneous inhibitory synaptic currents were recorded when the AMPA- and NMDA-receptors were blocked with NBQX and D-AP5 respectively. Together these two findings indicate that CA1 pyramidal cells have both functional excitatory and inhibitory synaptic inputs. The afferent excitatory synapses to the CA1 pyramidal cells were able to express long-term synaptic plasticity, this was tested using extracellular recordings. As seen in FIG. 4D two brief high frequency stimulations (two 100-impulse trains, 100 Hz, 20 sec apart) of the afferents induced a long-lasting increase in synaptic efficacy. Taken together these findings suggest that the CA1 pyramidal cells from mouse organotypic slices (div 11) display normal histological and electrophysiological properties, maintain both functional excitatory and inhibitory synaptic inputs and that these inputs are able to express synaptic plasticity.

Figure 5B:
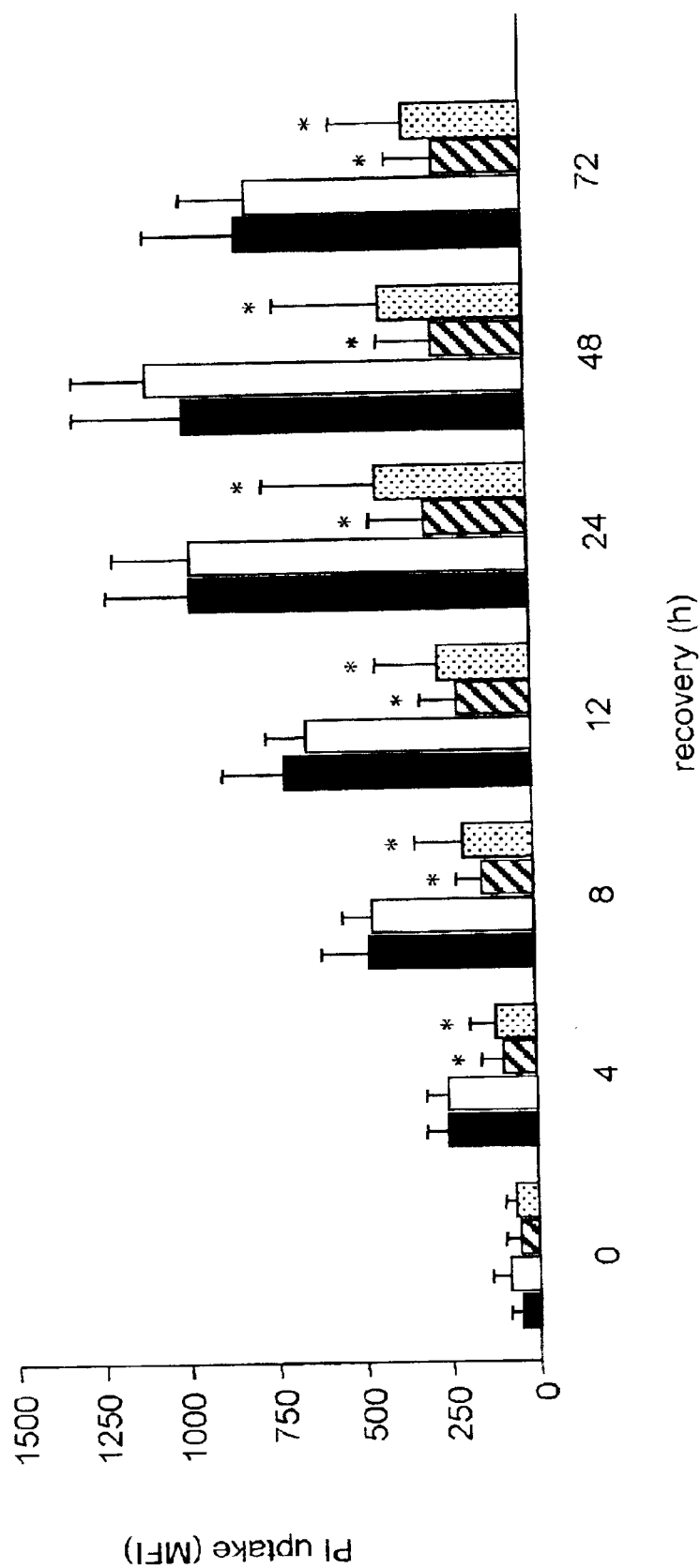
FIG. 5. The influence of the ionic composition of the OGD-medium on cell damage after OGD. (A) Representative groups of cultures subjected to 15-minute-OGD in glucose-free artificial cerebrospinal fluid (aCSF; 2.5 mM K$^+$, 2 mM Ca$^{2+}$, pH 7.4), aCSF with 70 mM K$^+$, aCSF with 0.3 mM Ca$^{2+}$ and aCSF with pH 6.8 respectively. Images were obtained after 48 hours of recovery. The damaged area and the density of propidium iodide (PI)-uptake is more extensive in the aCSF and aCSF with 70 mM K$^+$ groups compared to cultures subjected to aCSF with 0.3 mM Ca$^{2+}$ and aCSF with pH 6.8. (B) Cell damage development over time measured as mean PI-fluorescence in the standardized CA1-area of cultures exposed to 15-minute-OGD in aCSF (dark grey bars), aCSF with 70 mM K$^+$ (light grey bars), aCSF with 0.3 mM Ca$^{2+}$ (hatched bars) and aCSF with pH 6.8 (dotted bars) respectively. Bars show mean±SD. All groups were compared with the aCSF-group at the same time-point. Asterisk indicate significant level of $p<0.01$, ANOVA with Fischer's post-hoc test, n=18. Significantly less damage was seen in the groups subjected to OGD in aCSF with 0.3 mM Ca$^{2+}$ and aCSF with pH 6.8 compared to the groups subjected to OGD in aCSF or aCSF with 70 mM K$^+$. The group subjected to OGD in aCSF with 70 mM K$^+$ does not significantly differ from the group subjected to OGD in conventional aCSF.

Influence of potassium, calcium and hydrogen ions on the development of cell damage after OGD. Complete deprivation of oxygen and glucose for 15 minutes in glucose-free aCSF led to a homogenous uptake of PI in the CA1 region (FIG. 5A). PI-uptake was not restricted to the CA1-area as the CA3 area displayed significant PI uptake as well. The increase in PI-uptake in the CA1-area was rapid, clearly visible after 4 hours of recovery and increasing for 24 hours (FIG. 5B). The PI-fluorescence in the CA1 area was very dense and homogenous. As the aim was to establish an in vitro model resembling the in vivo ischemia conditions it was decided to change the concentration of potassium, calcium and hydrogen ions in the OGD-medium to those reported in vivo.

The contribution of the individual ions was first examined by modifying aCSF. The temporal development of damage and the density of PI-uptake in the CA1 region was similar when the potassium concentration was increased from 2.5 to 70 mM. However PI-uptake in the CA3 region also increased. A decrease in calcium to 0.3 mM significantly decreased cell damage. Lowering pH to 6.8 led to significantly less PI-uptake at all time points from 4 to 72 hours. In cultures subjected to OGD in aCSF with pH 6.8, the area in CA1 taking up PI was smaller compared to the aCSF treated group and was selective to the CA1 region. At 0.3 mM calcium and pH 6.8 no damage to CA3 was seen.

Figure 6A:
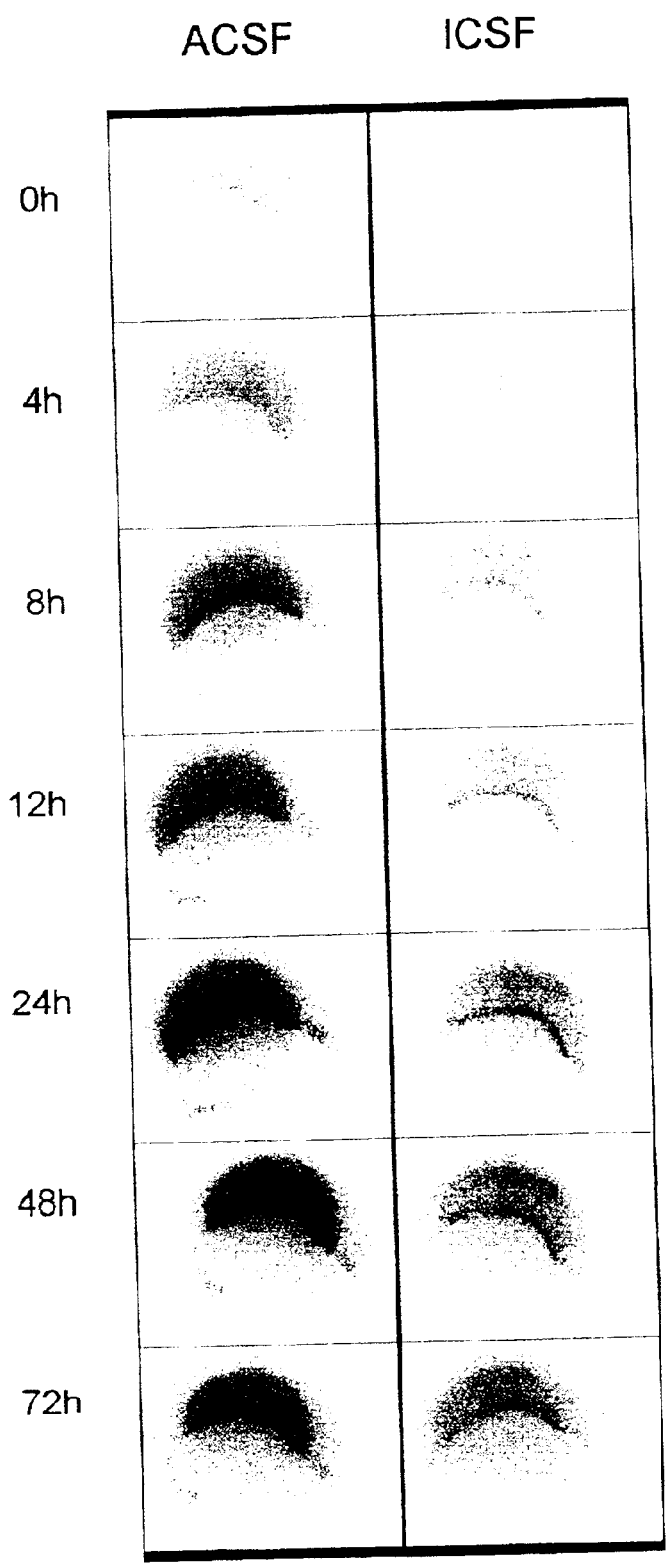
FIG. 6. Temporal development of cell damage after OGD in aCSF and iCSF. (A) Inverted fluorescent images of representative cultures showing the development of cell damage after 15-minute-OGD in glucose-free artificial cerebrospinal fluid (aCSF) and ischemic cerebrospinal fluid (iCSF), respectively. Cultures were stained with PI to show cell damage. The same culture is shown at 0, 4, 8, 12, 24, 48 and 72 hours of recovery. (B) Mean propidium iodide (PI)-intensity in the standardized CA1-area of cultures exposed to 15-minute-OGD in aCSF (black bars) or iCSF (grey bars) at different times of recovery. All groups were compared to their respective values obtained before OGD (0). Data are shown as means±SD with n=18 (* indicates $p<0.001$; ANOVA+Fischer post hoc test). aCSF-treated cultures displayed a significant increase in PI-intensity already after 4 hours of recovery whereas the iCSF-treated cultures did not differ significantly until after 8 hours of recovery. After 24 hours there was no further statistically significant increase of PI-intensity in the aCSF-treated group whereas the PI-intensity in the iCSF treated cultures continued to increase until 48 hours of recovery (p-values are shown in figure). PI-intensity is significantly higher in the aCSF versus iCSF treated group at all time points ($p<0.005$).
Figure 6B:
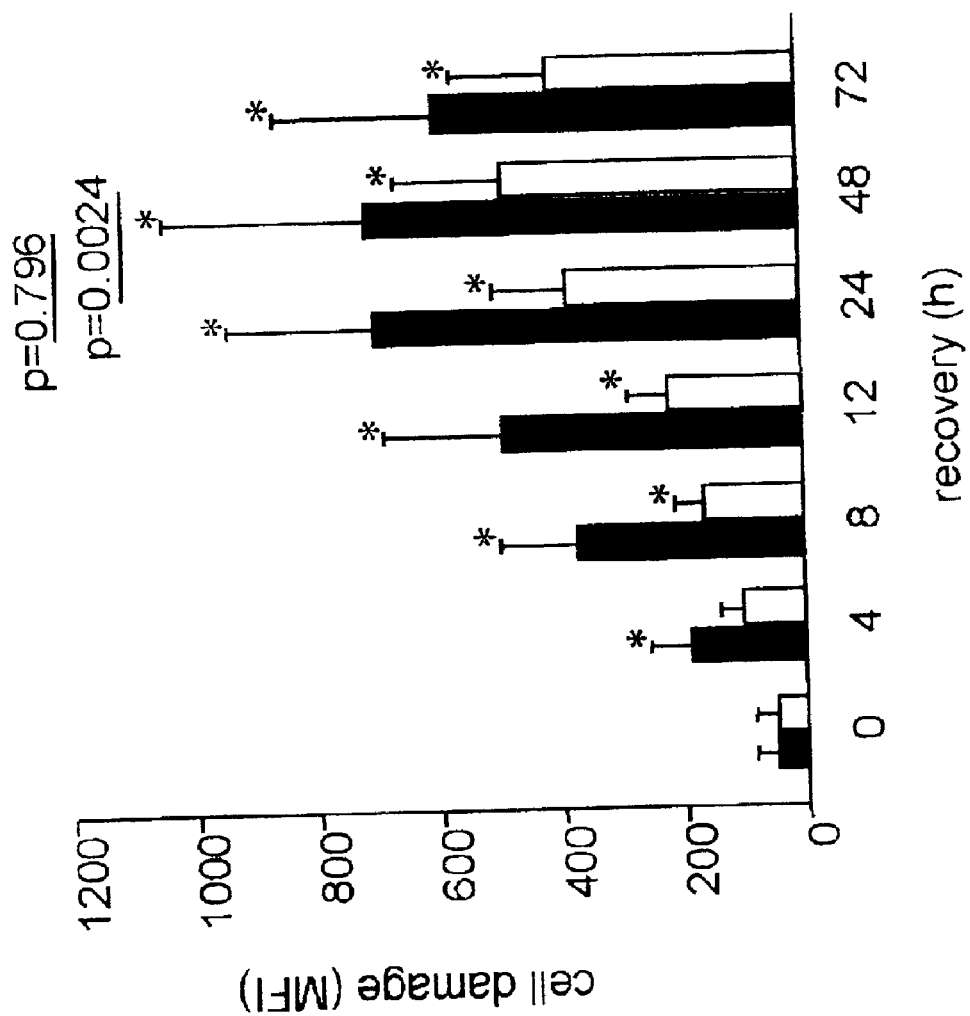

The ischemic cerebrospinal fluid (iCSF). By changing the OGD medium to 70 mM $K^+$, 0.3 mM $Ca^{2+}$ and pH to 6.8, and in addition decreasing $Na^+$ to 75 mM, the extracellular concentrations in the tissue cultures would be similar to those in the brain during complete ischemia. This glucose-free medium was called ischemic cerebrospinal fluid (iCSF). The development of cell damage after OGD in iCSF was compared to that in aCSF (FIG. 6). Cultures exposed to a 15-minute-OGD in iCSF developed a selective cell damage restricted to the CA1 area without damage to CA3 neurons damage. These cultures also displayed a slower development of cell damage than their acsf-treated counterparts. In acsf-treated cultures a significant increase in PI-uptake was seen already after 4 hours of recovery. Damage developed rapidly and there was no statistically significant increase in PI-uptake between 24 and 48 hours of recovery. In the iCSF-treated cultures on the other hand, a significant increase in PI-uptake was not found until after 8 hours of recovery and PI-intensity continued to increase significantly between 24 and 48 hours of recovery.

To investigate whether iCSF or the washing procedure in itself could be harmful to neurons, groups of cultures were incubated in iCSF and aCSF for 15 minutes following the same protocol as in the OGD-experiments but exchanging the anaerobic incubator for the regular $CO_2$-incubator. None of the groups displayed any elevated PI-uptake at 48 hours of recovery compared to culture controls.

Figure 7C:
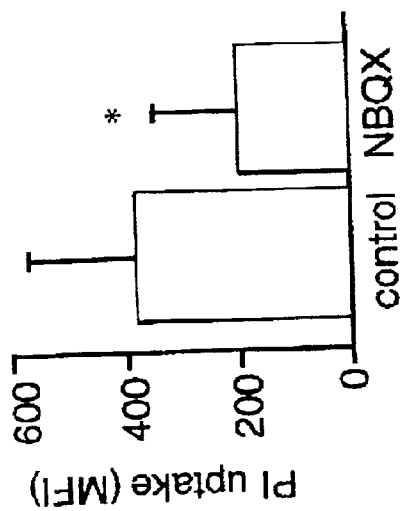
FIG. 7. Protective effect of glutamate antagonists. The glutamate antagonists MK-801 (20 $\mu$M) (A), D-AP5 (150 $\mu$M) (B) and NBQX (100 $\mu$M) (C) all provided significant (*$p<0.0001$, ANOVA+Fischers test, n=18–24) protective effect against 15-minute-OGD in iCSF. Control cultures were exposed to 15-minute-OGD in ICSF. Bars show mean (±SD) quantified PI-intensity in the CA1-area at 24 hours of recovery.
Figure 7B:
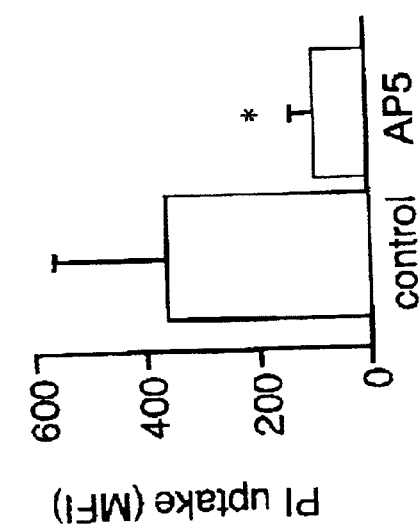
Figure 7A:
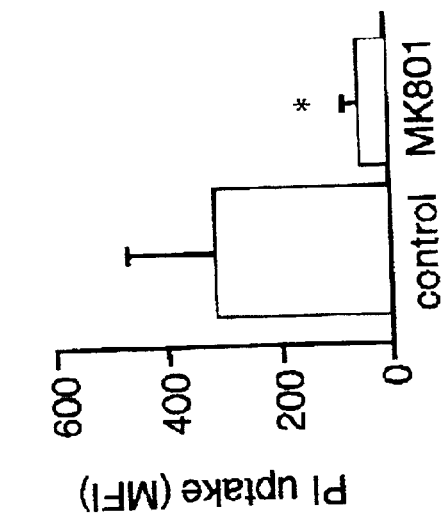

Cell damage was blocked with antagonist to NMDA and AMPA receptors. To investigate the involvement of glutamate receptors in the damage induced by OGD in iCSF, NMDA receptors were blocked with the non-competitive antagonist MK-801 and the competitive antagonist D-AP5. Pretreatment with 20 $\mu$M MK-801 for one hour before a 15-minute OGD in iCSF resulted in significantly (90%) less damage in the CA1 region at 24 hours of recovery compared to matched OGD-control cultures (FIG. 7A). A similar (70%) protective effect was seen when 150 $\mu$M D-AP5 was added to the culture medium one hour before OGD, to the iCSF during OGD and present throughout recovery (FIG. 7B). Involvement of AMPA-receptors was investigated with the competitive antagonist NBQX included in the medium from one hour before to 24 hours after a 15-minute-OGD. This resulted in a significant (50%) reduction of PI-uptake compared to controls (FIG. 7C).

Figure 8:
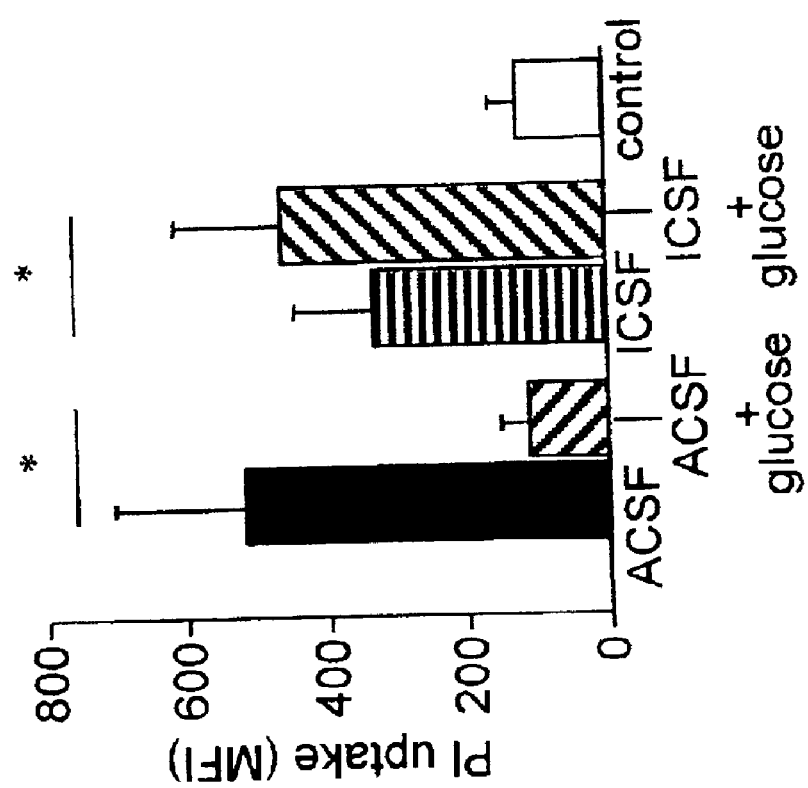
FIG. 8. Glucose decreases cell damage after hypoxia in aCSF but increases cell damage after hypoxia in iCSF. Addition of 40 mM glucose to the glucose-free artificial cerebrospinal fluid (aCSF) completely prevented cell-damage after 15-minute-hypoxia. Propidium iodide (PI)-intensity in the CA1-area of aCSF with 40 mM glucose treated cultures (light grey bar) did not differ from controls (white bar) and was significantly less than aCSF treated cultures (dark grey bar). The addition of 40 mM glucose to ischemic cerebrospinal fluid (iCSF) made cell damage in the CA1 area significantly worse following a 15-minute-hypoxia in iCSF alone. Results are derived from three different experiments and calculated by ANOVA with post hoc Fischer's test, n=18 for each group (*$p<0.0001$).

The presence of glucose during hypoxia in iCSF exacerbated cell damage. When aCSF was supplemented with 40 mM glucose (the glucose concentration of the culture medium) during a 15-minute-hypoxia, no cell damage was observed (FIG. 8). These glucose-supplemented hypoxia exposed cultures displayed the same level of PI-uptake in the CA1-area as control cultures kept in the $CO_2$-incubator throughout the experiment. In contrast, addition of 40 mM glucose to iCSF during a 15-minute-hypoxia had the opposite effect and resulted in significantly more PI-uptake in the CA1-area than the iCSF-OGD controls run in parallel. Measurements were made after 48 hours of recovery in all groups.

Hippocampal organotypic tissue cultures have been widely used to study ischemic, hypoxic, hypoglycaemic, oxidative and excitotoxic damage. In these experiments ischemia-like condition is induced by a combination of oxygen and glucose deprivation achieved by an anoxic atmosphere in combination with a glucose free medium, similarly as described for dissociated cell cultures, or by inhibition of oxidative phosphorylation using cyanide in combination with 2-deoxyglucose.

The present invention provides a model for OGD in mouse hippocampal organotypic tissue cultures that in many aspects resemble the tissue reaction to brain ischemia in vivo. The results show that the composition of the OGD-medium is of critical importance for the development of cell death after in vitro ischemia. By adapting the medium used during OGD to the pathophysiological concentrations of potassium, calcium and hydrogen ions measured in in vivo global ischemia the selectivity and temporal profile of damage seen in vivo could be mimicked.

For assessment of damage PI-uptake was used as a cell death indicator. In concordance with previous reports we could not see any harmful effects of PI on cell survival pi-fluorescence has been shown to correlate linearly with histologically defined neuronal damage as well as lactate dehydrogenase release. Also, PI staining correlated with histological evaluation of neuronal damage.

Cell death in the hippocampus in vivo, following moderate ischemia periods, is characterized by a selective and delayed neuronal damage in the CA1 region with recruitment of damage to CA3 region following prolonged ischemia. Selective vulnerability and delayed death of CA1 neurons after global ischemia have been described in gerbil and in rat. In mouse, 10 minutes of bilateral common carotid artery occlusion in combination with systemic hypotension resulted in delayed CA1 cell death occurring between 1 and 3 days of reperfusion. Thus, the development of cell damage following global ischemia seems to have a similar course of events in rat and mouse.

A selective and delayed cell death in the CA1 region, as seen in vivo, has so far not been reported in hippocampal organotypic cultures. Using rat hippocampal organotypic tissue cultures, several authors have reported a relative selectivity in cell death in CA1 following OGD. For example, cell damage in the CA1 region was twice that seen in the CA3 region of hippocampal organotypic tissue cultures after 30 minutes OGD. The development of cell death in cultures is generally faster than in vivo. A significant elevation of LDH two hours after OGD was found in neocortical cell cultures, and was maximal after 12–16 hours. In rat hippocampal organotypic tissue cultures elevation of PI-fluorescence in the CA1 area 6 hours after 60 minutes OGD was seen, that increased up to 24 hours of recovery.

Initial experiments were performed with aCSF as OGD medium. Cell death developed rapidly and that there was no clear selective CA1 damage. When the cultures were exposed to OGD for 15 min, cell death was seen in CA3 cells and dying cells were seen in CA1 already at 4 hrs of recovery. It was recognized that an important difference between the in vivo and in vitro experiments is the composition of the extracellular fluid. In most models of in vitro ischemia, glucose free aCSF or balanced salt solutions are used as medium during OGD. Because the size of the extracellular space in a culture, i.e. the volume of the medium, is several magnitudes larger than that in vivo the redistribution of ions during OGD due to membrane depolarisation will have a negligible effect on the extracellular ion concentrations. The intracellular ion concentrations during OGD will therefore be highly dependent of the ion content of the medium. The ion composition of aCSF is similar to the cerebro-spinal fluid of normal brains and evidently markedly different from the composition of the extracellular fluid in the brain during an ischemic insult. Thus to simulate the conditions during in vivo ischemia more closely, we have examined the effect of changing the concentrations of calcium, potassium and hydrogen ions.

The loss of ATP during ischemia results in a rundown of transmembrane ion gradients, leading to a rapid membrane depolarization (occurring within 1–2 minutes) due to the reversal of the sodium dependent ion transporters and the opening of voltage and agonist dependent ion channels. Using potassium selective electrodes, the potassium concentration in the extracellular space was found to increase to 70 mM during ischemia. When our cultures were placed in glucose free aCSF with a potassium concentration of 70 mM, a steep membrane depolarization occurred, similar to that seen in vivo. Still, under normoxic conditions incubation in 70 mM did not cause damage to the cultures. Also, cell damage in cultures exposed to 15-minute OGD in aCSF with 70 mM potassium was similar as in cultures exposed to OGD in aCSF (2.5 mM potassium). Clearly, high potassium levels during OGD did not aggravate cell damage.

Increased intracellular calcium ion levels play an important role in ischemic neuronal injury. When the cell is depolarized, and the calcium extrusion and sequestration mechanisms fail, the intracellular calcium concentration rise. Using calcium selective electrodes, the extracellular calcium concentration was found to fall to 0.1 mM or 0.2–0.3 mM during complete global ischemia. When OGD was performed in aCSF with 0.3 mM calcium, damage was significantly reduced compared to that seen with aCSF (2 mM calcium). Also, CA3 cells were not damaged. This neuroprotective effect of decreased calcium during OGD has previously been shown in cell cultures (Rothman, 1983) and in hippocampal organotypic tissue cultures.

During ischemia, the anaerobic glycolysis leads to lactic acid production and to a decrease in extracellular pH to 6.8–6.2. The magnitude of the drop in pH is depend on the preischemic plasma levels of glucose. Acidosis and hyperglycemia is well known to increase damage in vivo. However, in all in vitro systems reported so far, lowering of pH to 6.8 in the medium during OGD significantly reduces damage. This protective effect has been attributed to the fact that low pH inhibit NMDA receptors and thus protects against glutamate toxicity. By lowering the pH of incubation medium to 6.8, damage was significantly reduced in the CA1 and in the CA3 regions, also in our system. Interestingly, albeit selective to CA1 the damaged area was decreased.

By changing the ion composition of medium to that of the extracellular fluid in the brain during ischemia, the extent and development of cell death markedly change. With therefore defined a medium iCSF, that included 77 mM sodium 70 mM potassium, 0.3 mM calcium and a pH of 6.8, based on available data in the litterature. In this medium 15 min OGD caused selective CA1 damage with no CA3 damage. Also damage was delayed compared to when OGD was induced in aCSF.

Glutamate receptor blockade of both NMDA (using MK-801 and AP5) and non-NMDA (using NBQX) subtypes have repeatedly been shown to protect neurons in different ischemia models, both in vivo (focal ischemia) and in in vitro models using dissociated neuronal cultures as well as in organotypic hippocampal cultures. Also, in a mouse model of global ischemia MK-801 protected CA1 cells when given after the ischemic insult. Here we show that damage following 15 minutes of OGD in iCSF is mitigated by NMDA and AMPA receptor blockade, demonstrating that glutamate receptor activation contributes to the cell death process.

An important pathophysiological characteristic of ischemic brain damage is the aggravation of cell death by hyperglycemia. In rat models of global ischemia, hyperglycemia, established prior to the insult, aggravates the injury possibly through an acidosis related mechanism. The aggravating effect of hyperglycemia during ischemia in vivo, has so far not been reproduced in vitro. On the contrary, murine neocortical cell cultures survive 8 hours of anoxia in the presence of 20 mM glucose, but develop extensive damage when exposed to 30 minutes OGD. Also, in hippocampal organotypic rat cultures 60 minutes of OGD led to significant neuronal damage that was abolished when glucose was included in the medium. In concordance with these results we found that the presence of 40 mM glucose during anoxia in aCSF completely prevented cell death. Quite the opposite, glucose significantly aggravated neuronal death when present during anoxia in iCSF. This is to our knowledge the first demonstration that glucose may aggravate hypoxiccell death in vitro. Clearly, this model is useful to study the pathophysiological mechanisms behind the aggravating effect of hyperglycemia during ischemia, and will be the subject of further investigations.

What is claimed is:

1. An ischemic cell culture, comprising:
    a culture comprising hippocampal tissue, and a medium for simulation of ischemia, comprising potassium at a concentration of from about 50 mM to 90 mM; calcium at a concentration of from about 0.1 mM to 1 mM; NaCl at a concentration of from about 30–77 mM; at a pH of from 6.7 to 6.9,
wherein when said cells are exposed to said medium for a period of time sufficient to mimic the effects of ischemia in vivo the ischemic effects include a selective and delayed, glutamate receptor dependent cell death in the CA1 region.

2. The method according to claim 1, wherein said cells comprise a section of brain tissue.

3. An ischemic cell culture, comprising:
    a culture comprising hippocampal tissue, and a glucose free medium for simulation of ischemia, comprising potassium at a concentration of from about 50 mM to 90 mM; calcium at a concentration of from about 0.1 mM to 1 mM; at a pH of from 6.7 to 6.9,
wherein when said cells are exposed to said medium for a period of time sufficient to mimic the effects of ischemia in vivo the ischemic effects include a selective and delayed, glutamate receptor dependent cell death in the CA1 region.

4. The culture according to claim 1, wherein glucose is present in said medium.

5. A method of simulating ischemia in vitro, the method comprising:
    exposing a culture comprising hippocampal tissue to a medium for simulation of ischemia, said medium comprising potassium at a concentration of from about 50 mM to 90 mM; calcium at a concentration of from about 0.1 mM to 1 mM; at a pH from 6.7 to 6.9,
wherein when said cells are exposed to said medium for a period of time sufficient to mimic the effects of ischemia in vivo the ischemic effects include a selective and delayed, glutamate receptor dependent cell death in the CA1 region.

6. The method according to claim 1, wherein said cells comprise a section of brain tissue.

7. The method according to claim 1, wherein said medium is glucose free.

8. The method according to claim 1, wherein glucose is present in said medium.

9. A method for determining the effect of a candidate agent on ischemia, the method comprising:
    exposing a culture comprising hippocampal tissue to said candidate agent before, during, or after said cells are exposed to a medium for simulation of ischemia, said medium comprising potassium at a concentration of from about 50 mM to 90 mM; calcium at a concentration of from about 0.1 mM to 1 mM; at a pH of from 6.7 to 6.9 ,
    wherein when said cells are exposed to said medium for a period of time sufficient to mimic the effects of ischemia in vivo the ischemic effects include a selective and delayed, glutamate receptor dependent cell death in the CA1 region;
comparing at least one parameter of said cells in the presence of said candidate agent and in a control wherein said agent is absent.

10. The method according to claim 9, wherein said cells comprise a section of brain tissue.

11. The method according to claim 9, wherein said medium is glucose free.

12. The method according to claim 9, wherein glucose is present in said medium.

* * * * *